US012690885B2

(12) United States Patent
Zhao et al.

(10) Patent No.: US 12,690,885 B2
(45) Date of Patent: Jul. 28, 2026

(54) METHOD FOR GUIDING FLEXIBLE ELECTRODE AND SYSTEM FOR IMPLANTING FLEXIBLE ELECTRODE

(71) Applicant: SHANGHAI STAIRMED TECHNOLOGY CO., LTD., Shanghai (CN)

(72) Inventors: Zhengtuo Zhao, Shanghai (CN); Xue Li, Shanghai (CN); Yu Bao, Shanghai (CN)

(73) Assignee: SHANGHAI STAIRMED TECHNOLOGY CO., LTD., Shanghai (CN)

( * ) Notice: Subject to any disclaimer, the term of this patent is extended or adjusted under 35 U.S.C. 154(b) by 46 days.

(21) Appl. No.: 18/877,005

(22) PCT Filed: Jun. 29, 2022

(86) PCT No.: PCT/CN2022/102321
§ 371 (c)(1),
(2) Date: Dec. 19, 2024

(87) PCT Pub. No.: WO2023/245706
PCT Pub. Date: Dec. 28, 2023

(65) Prior Publication Data
US 2025/0375216 A1      Dec. 11, 2025

(30) Foreign Application Priority Data
Jun. 20, 2022    (CN) ......................... 202210697105.1

(51) Int. Cl.
*A61B 17/34*        (2006.01)

(52) U.S. Cl.
CPC ................................ *A61B 17/3403* (2013.01)

(58) Field of Classification Search
CPC .................................................. A61B 17/3403
See application file for complete search history.

(56) References Cited

FOREIGN PATENT DOCUMENTS

| CN | 108903916 A | 11/2018 |
|----|-------------|---------|
| CN | 112641448 A | 4/2021 |
| CN | 112999511 A | 6/2021 |
| CN | 113041496 A | 6/2021 |
| CN | 114469117 A | 5/2022 |
| CN | 114631822 A | 6/2022 |
| JP | 2009254902 A | 11/2009 |

OTHER PUBLICATIONS

International Search Report and Written Opinion from International Application No. PCT/CN2022/102321.

*Primary Examiner* — Lindsey G Wehrheim
(74) *Attorney, Agent, or Firm* — Dilworth & Barrese, LLP.; Michael J. Musella, Esq.

(57) ABSTRACT

The present disclosure relates to a method for guiding a flexible electrode, comprising: engaging a guide device with a first engagement part of the flexible electrode, and enabling a first section of the flexible electrode adjacent to the first engagement part to be located near the guide device; spraying a liquid to the flexible electrode, such that at least the first section of the flexible electrode is attached to a first surface of the guide device; and using the guide device to guide the flexible electrode. The present disclosure further relates to a system for implanting a flexible electrode.

20 Claims, 6 Drawing Sheets the needle-shaped portion of the guide device flexible electrode liquid spraying device electrode substrate    support plate    electrode fixing device

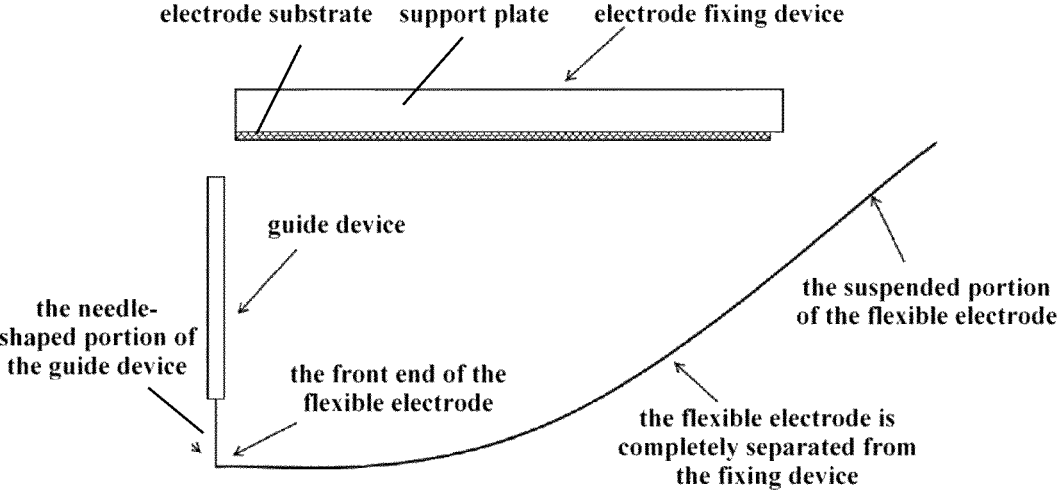

guide device the needle-
shaped portion of
the guide device the front end of the
flexible electrode the suspended portion
of the flexible electrode the flexible electrode is
completely separated from
the fixing device

Fig. 1C

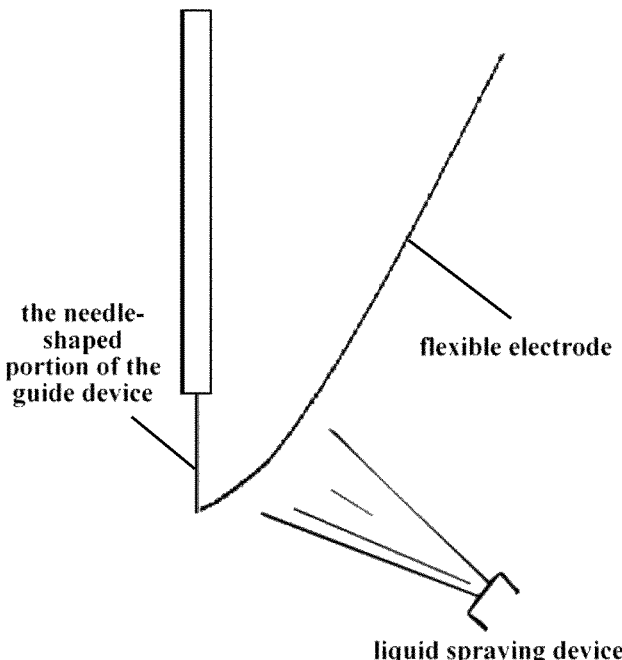

the needle-
shaped
portion of the
guide device flexible electrode liquid spraying device

Fig. 1D

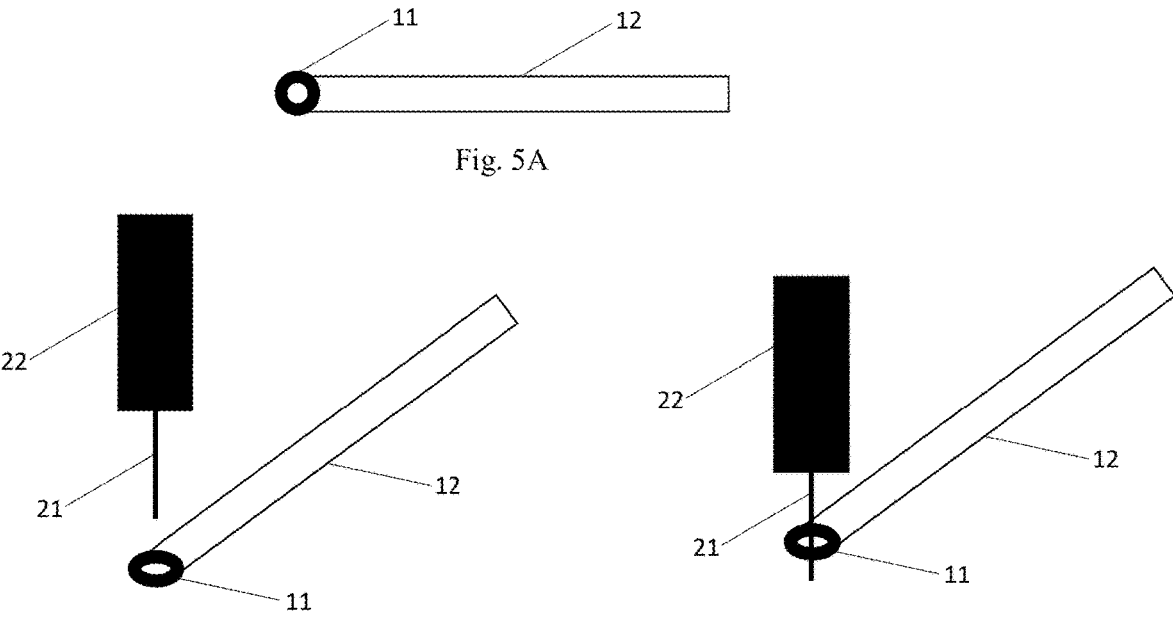
Fig. 5A
Fig. 5B
Fig. 5C
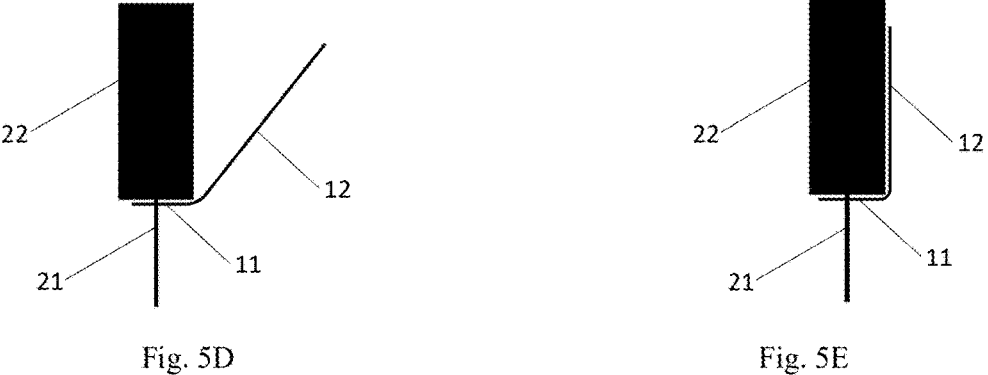
Fig. 5D
Fig. 5E

METHOD FOR GUIDING FLEXIBLE ELECTRODE AND SYSTEM FOR IMPLANTING FLEXIBLE ELECTRODE

TECHNICAL FIELD

The present disclosure relates to a method for guiding a flexible electrode and a system for implanting a flexible electrode.

BACKGROUND

Invasive brain-computer interface is to implant electrodes that can measure and release electrical signals into the brain, and decode neural signals through the detected electrical signals; it can also release signals through implanted electrodes to regulate the brain and then regulate the life activities of the whole organism. The decoding of electrical signals collected by electrodes can be applied to prosthetic control to help disabled people recover their limb functions; the release of electrical signals of electrodes can be applied to the regulation of neurological diseases such as epilepsy.

In the application of invasive brain-computer interface, electrode implantation is a very difficult problem. In order to reduce rejection reaction of electrode in vivo and reduce implantation damage, flexible electrodes have been developed. However, flexible electrodes are more difficult to implant because of their "flexibility" characteristics.

SUMMARY

One of the objects of the present disclosure is to provide a method for guiding a flexible electrode and a system for implanting a flexible electrode.

According to a first aspect of the present disclosure, a method for guiding a flexible electrode is provided, comprising: engaging a guide device with a first engagement part of the flexible electrode, and enabling a first section of the flexible electrode adjacent to the first engagement part to be located near the guide device; spraying a liquid to the flexible electrode, such that at least the first section of the flexible electrode is attached to a first surface of the guide device; and guiding the flexible electrode with the guide device.

According to a second aspect of the present disclosure, a method for guiding a flexible electrode is provided, comprising: applying a pulling force to a first end of the flexible electrode with a guide device to at least partially separate the flexible electrode from a flexible electrode fixing device; spraying a liquid to the flexible electrode, such that at least a first section of the flexible electrode comes near to the guide device and is attached to the guide device; and guiding the flexible electrode with the guide device to a target position.

According to a third aspect of the present disclosure, a method for guiding a flexible electrode is provided, which comprises a first end configured to be adapted for engagement with a guide device and a first section connected to the first end, wherein the first section has a proximal end adjacent to the first end and a distal end away from the first end, wherein the method comprises: engaging the guide device with the first end and causing the first section to be suspended from a fixing device via the distal end of the first section; spraying a liquid to the flexible electrode in a direction generally from the first section to the guide device, such that at least the first section of the flexible electrode is attached to the guide device; and guiding the flexible electrode with the guide device.

According to a fourth aspect of the present disclosure, a system for implanting a flexible electrode is provided, comprising: a flexible electrode fixing device located on one side of an implantation target, wherein the fixing device is configured to fix the flexible electrode to be implanted; a driving device, which is so configured, that it can be positioned generally on an extension line from the implantation target to the fixing device and to drive a guide device for guiding the flexible electrode to move generally toward the target, wherein the driving device is further configured to drive the guide device to move to pull the flexible electrode after the guide device engages with a first engagement part of the flexible electrode fixed on the fixing device, thereby at least partially separating the flexible electrode from the fixing device; and a liquid spraying device positioned facing a first section in a portion of the flexible electrode, which is separated from the fixing device, and facing the guide device, wherein the liquid spraying device is configured to spray a liquid having a spraying force generally directed from the first section of the flexible electrode to the guide device, so that at least the first section of the flexible electrode is attached to the guide device under the action of the sprayed liquid, wherein the driving device is further configured to continue driving the guide device to move after at least the first section of the flexible electrode is attached to the guide device, thereby implanting the first engagement part of the flexible electrode and at least a portion of the first section adjacent to the first engagement part into the target.

Other features and advantages of the present disclosure will become apparent from the following detailed description of exemplary embodiments of the present disclosure with reference to the accompanying drawings.

BRIEF DESCRIPTION OF DRAWINGS

The accompanying drawings, which form a part of the description, describe embodiments of the present disclosure and, together with the description, serve to explain the principles of the present disclosure.

FIG. 1A-FIG. 1E are schematic diagrams of a method for guiding a flexible electrode according to an embodiment of the present disclosure.

FIG. 5A-FIG. 5E are schematic diagrams of a method for guiding a flexible electrode according to an embodiment of the present disclosure.

Figure 1A:
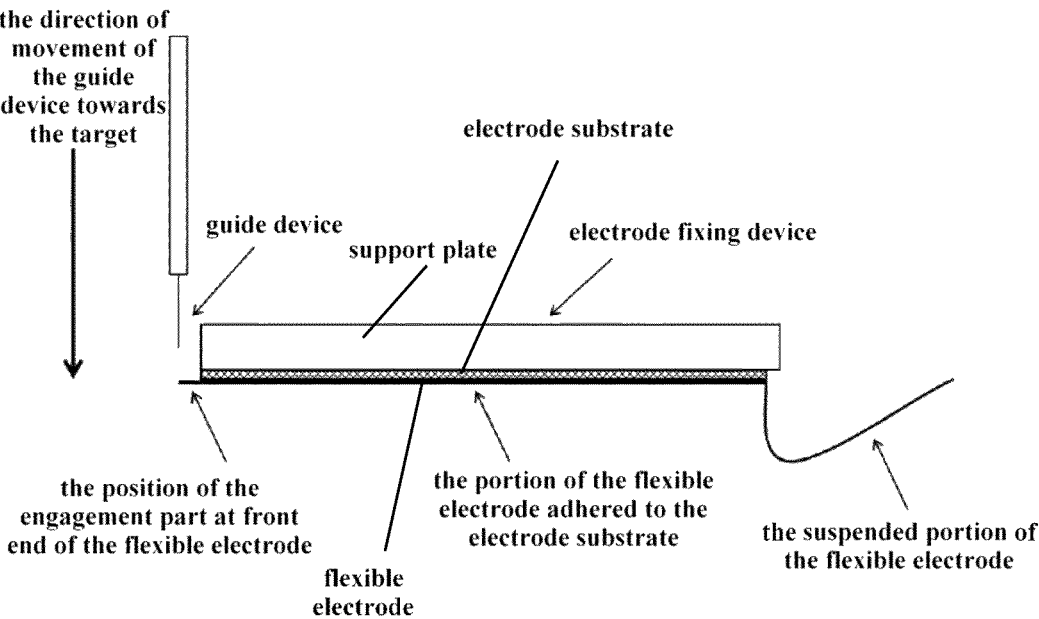

Note that, in the embodiments described below, the same parts or parts having the same functions may be denoted by the same reference numbers in different drawings, and redundant description thereof may be omitted. In some cases, similar numbers and letters are used to represent similar items, and therefore, once an item is defined in one figure, it does not need to be further discussed in subsequent figures.

For ease of understanding, the positions, dimensions, ranges, and the like of each configuration shown in the drawings and the like may not indicate actual positions, dimensions, ranges, and the like. Therefore, the present disclosure is not limited to the positions, dimensions, ranges, and the like disclosed in the drawings and the like.

DETAILED DESCRIPTION

The present disclosure will be described below with reference to the accompanying drawings, in which several embodiments of the present disclosure are illustrated. It should be understood, however, that the present disclosure may be presented in many different ways and is not limited to the embodiments described below; in fact, the embodiments described below are intended to complete the disclosure of the present disclosure and fully illustrate the scope of protection of the present disclosure to those skilled in the art. It should also be understood that the embodiments disclosed herein can be combined in various ways to provide more additional embodiments.

It should be understood that the terms used herein are used to describe specific embodiments only and are not intended to limit the scope of the present disclosure. All terms (including technical and scientific terms) used herein have the meanings commonly understood by those skilled in the art unless otherwise defined. For conciseness and/or clarity, well-known functions or structures may not be described in detail.

Herein, when an element is said to be "on" another element, "attached" to another element, "connected" to another element, "coupled" to another element, or "contacting" another element, or the like, the element may be directly on, attached to, connected to, coupled to, or contacting the other element, or intermediate elements may be present. In contrast, when an element is said to be "directly" "on" another element, "directly attached" to another element, "directly connected" to another element, "directly coupled" to another element, or "directly contacting" another element, there will be no intermediate elements. Herein, one feature is arranged "adjacent" to another feature, which may mean that one feature has a portion that overlaps an adjacent feature or a portion that is located above or below an adjacent feature.

Herein, reference may be made to elements or nodes or features that are "coupled" together. Unless explicitly stated otherwise, "coupled" means that one element/node/feature may be mechanically, electrically, logically, or otherwise coupled to another element/node/feature in a direct or indirect manner to allow interaction, even if the two features may not be directly connected. That is, "coupled" is intended to include direct and indirect joining of elements or other features, including joining with one or more intermediate elements.

Herein, spatial relationship terms such as "above", "below", "left", "right", "front", "rear", "high", "low" etc. may illustrate the relationship of one feature to another feature in the drawings. It should be understood that the spatial relationship terms encompass different orientations of the device in use or operation in addition to the orientations shown in the figures. For example, when the device in the drawings is inverted, a feature that was previously described as being "below" other features may be described as being "above" other features. The device may also be oriented in other ways (rotated 90 degrees or in other orientations), where the relative spatial relationships will be interpreted accordingly.

Herein, the term "A or B" includes "A and B" and "A or B" and does not exclusively include only "A" or only "B" unless specifically stated otherwise.

Herein, the term "exemplary" means "used as an example, instance, or illustration" rather than as a "model" to be precisely replicated. Any implementation exemplarily described herein is not necessarily to be construed as preferred or advantageous over other implementations. Moreover, the present disclosure is not limited by any stated or implied theory set forth in the above-described technical field, background, summary, or detailed description.

Herein, the term "substantially" is meant to include any minor variation caused by defects in design or manufacture, tolerances of devices or elements, environmental influences, and/or other factors. The term "substantially" also allows for differences from perfect or ideal situations due to parasitic effects, noise, and other practical considerations that may exist in actual implementations.

In addition, similar terms such as "first" and "second" may also be used herein for reference purposes only, and are therefore not intended to be limiting. For example, the words "first", "second" and other such numerical words referring to structures or elements do not imply order or sequence unless the context clearly dictates otherwise.

It should also be understood that the word "comprising/including", when used herein, indicates the presence of the indicated features, steps, operations, units, and/or components, but does not preclude the presence or addition of one or more other features, steps, operations, units, and/or components, and/or combinations thereof.

The present disclosure provides methods for guiding a flexible electrode and systems for implanting a flexible electrode. The flexible electrode includes a front end that can be implanted into a target (such as biological tissue) and a rear end for connecting circuitry. The front end of the flexible electrode may collect electrical signals from the target and transmit the collected electrical signals to a circuit connected to the rear end of the flexible electrode through a conductor in the flexible electrode. Furthermore, the rear end of the flexible electrode may receive electrical signals from the circuit to which it is connected and transmit the received electrical signals to the front end of the flexible electrode through a conductor in the flexible electrode, thereby applying the electrical signals to the implanted target.

The flexible electrode to which the present disclosure relates extends between its front end to its rear end and has good flexibility, or at least in a section adjacent to its front end (e.g., a section for implantation target), in order to reduce damage to the tissue of the implantation target. Furthermore, also in order to reduce damage to the tissue of the implantation target, both the width and thickness of the flexible electrode are configured to have very small dimensions, for example, the width and thickness on the order of nanometers or micrometers; meanwhile, in order to facilitate the establishment of an electrical connection between the implantation target and the electrical circuit, the flexible electrode may have a length that is several orders of magnitude greater than its width and thickness, for example a length on the order of centimeters. Thus, the flexible electrode to which the present disclosure relates may be configured to be ribbon-shaped or filament-shaped, or at least a section thereof for implantation target may be configured to be ribbon-shaped or filament-shaped. Therefore, the flexible electrode to which the present disclosure relates may also be referred to as an electrode filament or a flexible electrode filament.

The flexible electrode to which the present disclosure relates includes an engagement part. The engagement part is configured to be able to engage with the guide device, so that the guide device guides the flexible electrode. FIG. 5A shows an example of a partial section of the flexible electrode adjacent to the front end from a plan view, and FIG. 5B and FIG. 5C show the example from a perspective view, and FIG. 5D and FIG. 5E from a side view, respectively. In this example, the front end of the flexible electrode is configured to have a ring-shaped portion 11, which can engage with the guide device and can therefore also be referred to as the engagement part 11 of the flexible electrode. The guide device may be configured to have a needle-shaped portion so as to pass at least partially through the engagement part 11 to engage with the flexible electrode. FIG. 5B-FIG. 5E also show an example of a needle-shaped portion of the guide device. In this example, the needle-shaped portion of the guide device comprises a first portion 21 having an outer diameter smaller than the inner diameter of the ring-shaped portion of the engagement part 11 and a second portion 22 having an outer diameter larger than the inner diameter of the ring-shaped portion of the engagement part 11. For simplicity, the second portion 22 of the needle-shaped portion shown in FIG. 5B to FIG. 5E may be only partial, i.e. only the section of the second portion 22 adjacent to the first portion 21 may be shown, and in practical implementation, the second portion 22 may also comprise a longer section extending upwardly.

FIG. 5B-FIG. 5E also illustrate an example in which the needle-shaped portion of the guide device and the flexible electrode are engaged. Since the first portion 21 is smaller than the inner diameter of the engagement part 11 and the second portion 22 is larger than the inner diameter of the engagement part 11, as shown in FIG. 5C, the first portion 21 of the needle-shaped portion of the guide device can pass through the ring-shaped engagement part 11 and the second portion 22 cannot pass through the ring-shaped engagement part 11; and as shown in FIG. 5D, after the first portion 21 passes through the engagement part 11, the guide device continues moving downward (with respect to the direction shown in the figure), so that the engagement part 11 of the flexible electrode is stopped between the first portion 21 and the second portion 22, so that the guide device can engage with the flexible electrode through the engagement part 11.

After engagement of the guide device with the flexible electrode, the guide device may guide the position of the flexible electrode, i.e. guide the flexible electrode from the first position to the second position. For example, with respect to the direction shown in the figure, the guidance is performed in the up-down direction, the left-right direction, and/or the direction perpendicular to the paper surface. In one example, the guide device guides the flexible electrode to implant the flexible electrode into the target. After engagement of the guide device with the flexible electrode, the guide device may continue moving (with respect to the direction shown in the figure) downward (for example driven by a driving device (not shown)) until at least part of the first portion 21 and the second portion 22 of the guide device enters the target, thereby implanting the engagement part 11 of the flexible electrode and at least the following portion of the section 12 adjacent to the engagement part 11 into the target, wherein said portion is connected to the engagement part 11. The inventors of the present application have found through research that, as shown in FIG. 5D, the section 12 of the flexible electrode is in a obliquely pulled state with respect to the longitudinal axis of the guide device, and if implanted in this state, it may cause large incision damage to the biological tissue of the target; this technical problem can be solved if at least the portion of the section 12 of the flexible electrode connected to the engagement part 11 can be attached to the guide device (for example, on the front section of the second portion 22 of the guide device), as shown in FIG. 5E. Therefore, the inventors of the present application have further studied and proposed the technical solution of the present disclosure, including methods for guiding a flexible electrode and a system for implanting a flexible electrode.

FIG. 1A-FIG. 1E are schematic diagrams of a method for guiding a flexible electrode according to an embodiment of the present disclosure. Also shown in these schematic diagrams are at least part of a system for implanting a flexible electrode according to an embodiment of the present disclosure, and states of the system and the flexible electrode when carrying out the steps of the method according to an embodiment of the present disclosure. As shown, the system for implanting a flexible electrode according to an embodiment of the present disclosure includes an electrode fixing device for fixing the flexible electrode to be implanted, a driving device for driving the guide device to move, and a liquid spraying device (as shown in FIG. 1D).

With respect to the direction shown in the figure, the implantation target is located below the system for implanting the flexible electrode, i.e. the electrode fixing device is located on the upper side of the implantation target. The electrode fixing device includes a support plate that can detachably fix the electrode substrate on the surface of the support plate adjacent to (or facing) the target. The flexible electrode may be adhered to the electrode substrate so as to be fixed on the support plate. Since the flexible electrode has greater flexibility and less mechanical strength, it is not convenient to be fixed on the support plate, and therefore an electrode substrate having a hardness higher than that of the flexible electrode can be used. The electrode substrate may be made of a high molecular polymer and fabricated with the flexible electrode to provide a limit and support for the flexible electrode before being implanted into the target. In implementation, a plurality of flexible electrodes are typically formed together in batches, and such a plurality of flexible electrodes may be formed to be adhered side by side on the electrode substrate. According to the need for implantation, one flexible electrode of the plurality of flexible electrodes may be implanted into the target, or several flexible electrodes of the plurality of flexible electrodes may be sequentially implanted into the target. As shown in FIG. 1A, the front section of the flexible electrode is arranged on the electrode fixing device and such that the engagement part of the flexible electrode at the front end protrudes from the electrode fixing device so as to engage with the guide device. After the flexible electrode is fixed on the electrode fixing device, between the front section and the rear section of the flexible electrode for connection to the circuit, there is a state in which a portion of the section (hereinafter referred to as a "rear section") is suspended in a non-tensioned state (as the "suspended portion" shown in the figure).

Figure 1B:
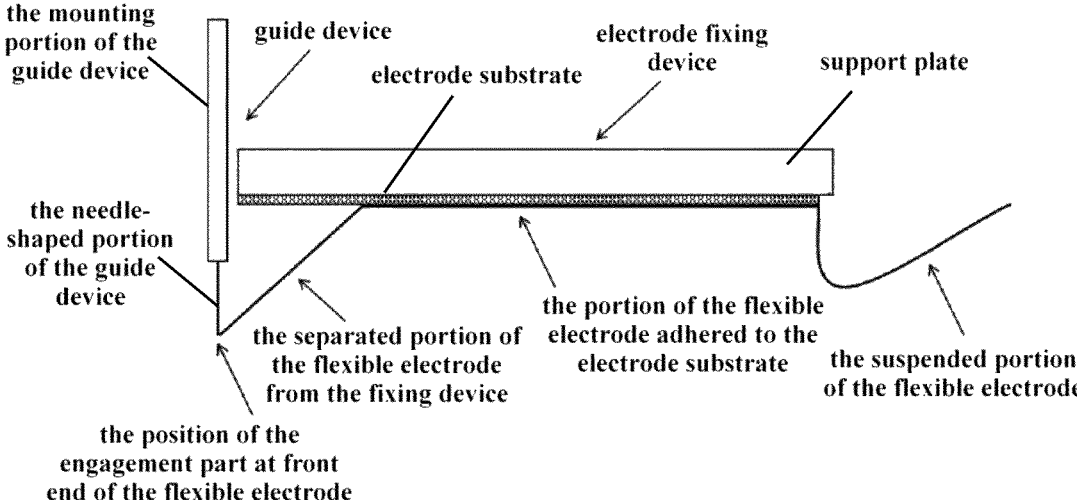

A driving device (not shown) may be positioned generally on the extension line from the implantation target to the electrode fixing device and drive the guide device for guiding the flexible electrode to move generally towards the target. As shown, the guide device may include a needle-shaped portion located at the end of the guide device (see FIG. 5B to FIG. 5E for a structural example of the needle-shaped portion) and a mounting portion for mounting the needle-shaped portion, and the needle-shaped portion may be mounted on the mounting portion by, for example, adhesive or socket. The driving device may be positioned at the top end of the mounting portion to drive the needle-shaped portion via driving the mounting portion to move. After the guide device engages with the engagement part of the flexible electrode fixed on the fixing device, the driving device drives the guide device to continue, for example, moving downward to pull the flexible electrode, i.e. to apply a pulling force to the front end of the flexible electrode, thereby at least partially separating the flexible electrode from the fixing device, as shown in FIG. 1B. The guide device may continue moving downward toward the target under the drive of the driving device to continue applying a pulling force to the flexible electrode through the front end of the flexible electrode, so that the flexible electrode may be completely separated from the electrode fixing device, as shown in FIG. 1C. Since the rear section of the flexible electrode is suspended (not tightly fixed on the electrode fixing device) and is in a non-tensioned state, after the flexible electrode is completely separated from the electrode fixing device, the part between the front end of the flexible electrode and its rear end (not shown, referring to the end for connecting the circuit) is also suspended in a non-tensioned state.

Figure 1E:
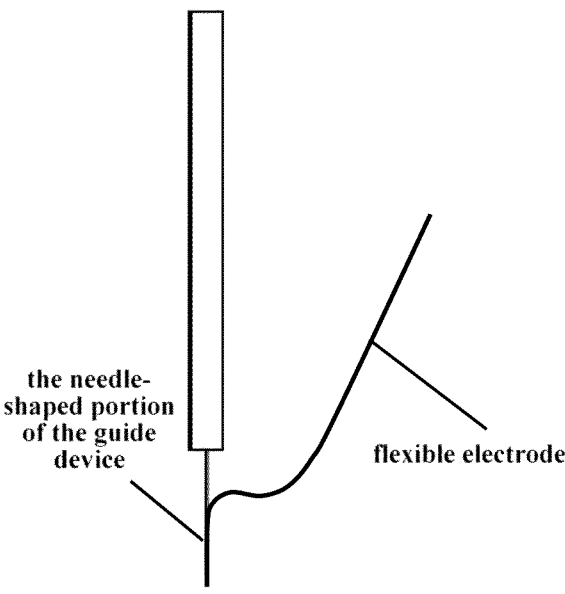
Figure 2A:
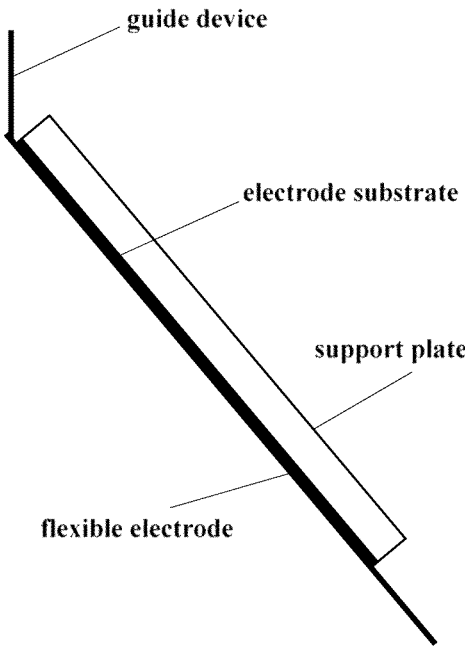
FIG. 2A-FIG. 2D are schematic diagrams of a method for guiding a flexible electrode according to an embodiment of the present disclosure.
Figure 2B:
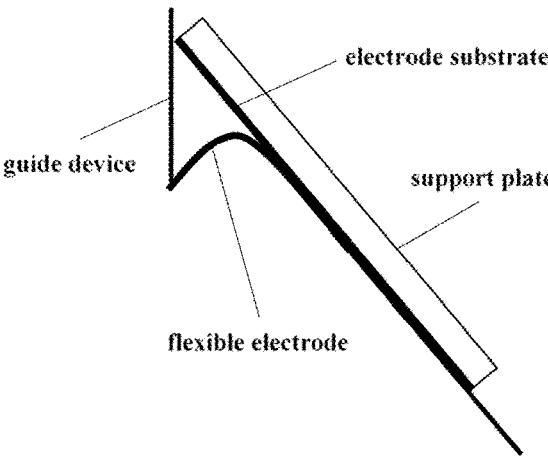
Figure 2C:
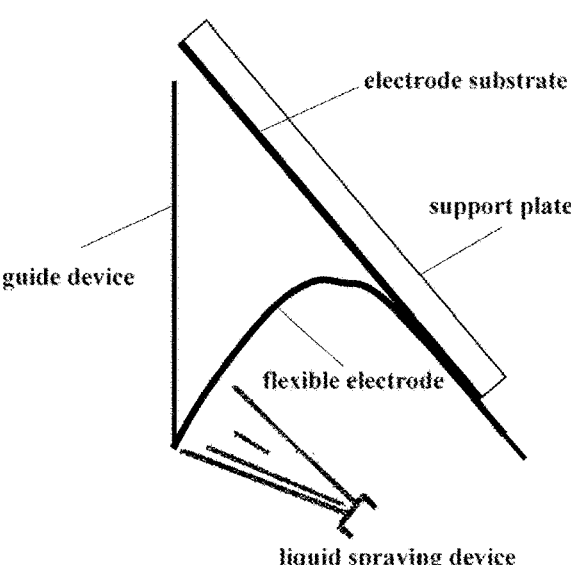
Figure 2D:
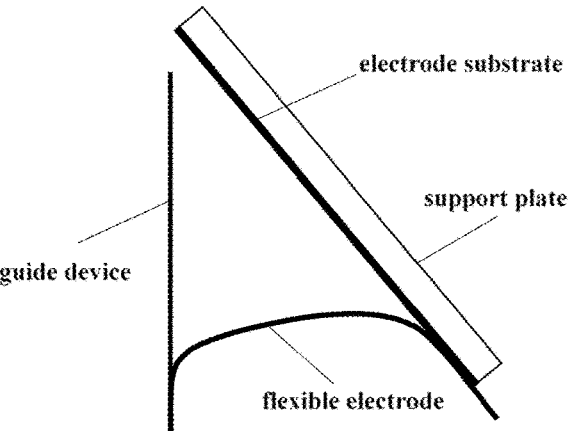

The liquid spraying device may be positioned facing a portion of the flexible electrode separated from the fixing device (in particular facing the section portion adjacent to the front end) and facing the guide device, and the liquid spraying device may be positioned to be able to spray a liquid having a spraying force generally directed from the section portion of the flexible electrode adjacent to the front end to the guide device, as shown in FIG. 1D, so that at least the section portion of the flexible electrode adjacent to the front end is attached to the guide device under the action of the sprayed liquid, as shown in FIG. 1E. In some embodiments, the liquid spraying device is an atomized spray device, such that the liquid is sprayed in an atomized state. The sprayed liquid may comprise pure water or a solution suitable for the target. In some embodiments, the guide device is configured to at least partially have a smooth surface, so that the flexible electrode is attached to the smooth surface. The smooth surface may be planar or curved. The respective section of the flexible electrode comes near to the guide device under the action of the spraying force of the liquid spraying and is attached to the guide device under the action of the surface tension of the sprayed liquid. In some embodiments, the liquid spraying device may be positioned to spray obliquely upward, as shown in FIG. 1D, so that the spraying force of the sprayed liquid has a direction generally from the proximal end of the section of the flexible electrode adjacent to the front end (i.e., one end adjacent to the engagement part) to the distal section of the guide device (i.e., the section away from the engagement part). After at least the section of the flexible electrode adjacent to the front end is attached to the guide device, the driving device may continue driving the guide device to move to implant the engagement part of the flexible electrode and at least the following portion of the section attached to the guide device into the target, wherein said portion is adjacent to the engagement part.

By providing the liquid spraying device so that at least a section portion of the flexible electrode adjacent to the front end is attached to the guide device, it is possible to avoid forming a large incision damage to the biological tissue of the target. In addition, further technical effects can be brought about by spraying the liquid. After the guide device engages with the engagement part of the flexible electrode fixed on the fixing device, and after the guide device completely separates the flexible electrode from the electrode fixing device, as shown in FIG. 1C, the flexible electrode, under the influence of its own gravity, may cause the engagement part of the flexible electrode to fall off from the guide device, resulting in undesirable consequences of separation of the flexible electrode from the guide device. However, after the flexible electrode is attached to the guide device by spraying the liquid, i.e. after the flexible electrode is in the state shown in FIG. 1E, the engagement between the flexible electrode and the guide device can be strengthened to prevent the flexible electrode from falling off from the guide device due to the gravity of the electrode itself.

Figure 3:
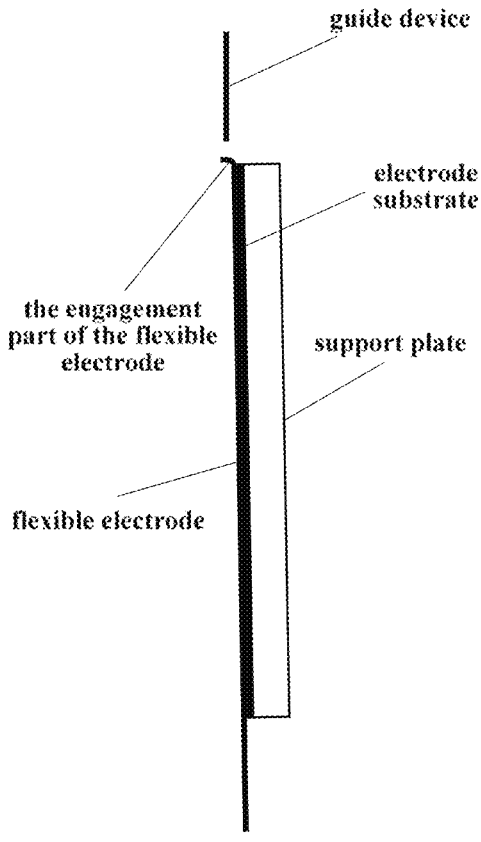
FIG. 3 is a schematic diagram of a method for guiding a flexible electrode according to an embodiment of the present disclosure.

In some embodiments, a sprayed liquid may be applied to the flexible electrode without the flexible electrode being completely separated from the electrode fixing device, so that the flexible electrode is attached to the guide device. FIG. 2A-FIG. 2D are schematic diagrams of a method for guiding a flexible electrode according to an embodiment of the present disclosure. In these embodiments, the support plate of the electrode fixing device is positioned at an angle to the horizontal plane, unlike the nearly horizontal placement in the embodiment described above. The guide device engages with the flexible electrode at the front end of the flexible electrode and drives the front end of the flexible electrode to move downward, thereby pulling the flexible electrode from the electrode substrate beginning with the front end of the flexible electrode, so that the front section of the flexible electrode is separated from the electrode substrate, but the rear section of the flexible electrode remains adhered to the electrode substrate and is suspended from the electrode fixing device. The liquid spraying device sprays a liquid having a spraying force generally directed from a section portion of the flexible electrode adjacent to the front end to the guide device, such that at least the section portion of the flexible electrode adjacent to the front end is attached to the guide device under the action of the sprayed liquid. It should be understood that the angle of the support plate of the electrode fixing device to the horizontal plane may also be substantially perpendicular, as shown in FIG. 3.

Figure 4:
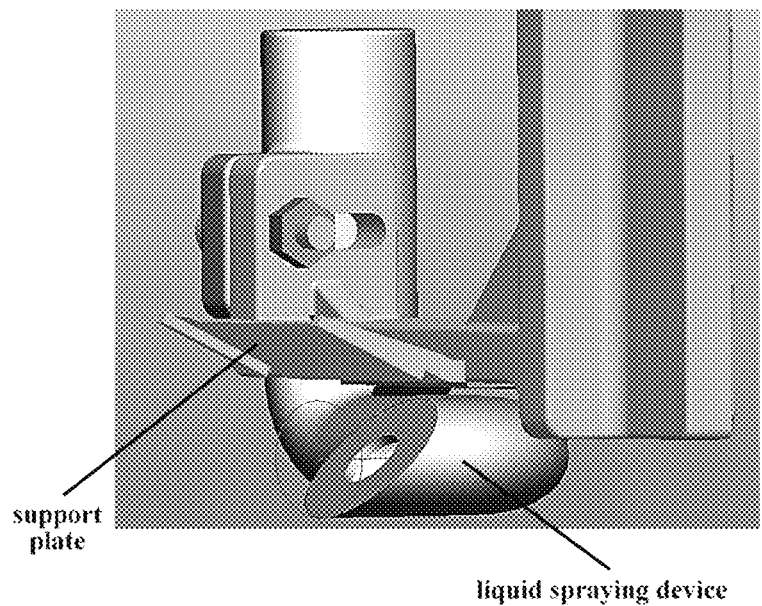
FIG. 4 is a schematic diagram of at least a portion of a system for implanting a flexible electrode according to an embodiment of the present disclosure.

In the above embodiments, systems for implanting flexible electrodes are all shown schematically. FIG. 4 shows one implementation of at least part of a system for implanting a flexible electrode, wherein at least the support plate of the electrode fixing device and the liquid spraying device are shown. It should be understood that FIG. 4 is for illustrative purposes only, and implementation of a system for implanting a flexible electrode according to an embodiment of the present disclosure is not limited thereto.

Although some specific embodiments of the present disclosure have been described in detail by way of examples, those skilled in the art should understand that the above examples are for illustration only and are not intended to limit the scope of the present disclosure. The various embodiments disclosed herein may be combined in any way without departing from the spirit and scope of the present disclosure. Those skilled in the art will also understand that various modifications can be made to the embodiments without departing from the scope and spirit of the present disclosure. The scope of the disclosure is defined by the appended claims.

The invention claimed is:

1. A method for guiding a flexible electrode, comprising:
engaging a guide device with a first engagement part of
the flexible electrode, and enabling a first section of the flexible electrode adjacent to the first engagement part to be located near the guide device;

spraying a liquid to the flexible electrode, such that at least the first section of the flexible electrode is attached to a first surface of the guide device; and guiding the flexible electrode with the guide device.

2. The method according to claim 1, wherein the liquid is sprayed in an atomized state, or wherein the liquid comprises pure water.

3. The method according to claim 1, wherein the first section of the flexible electrode comes near to the guide device under the action of the spraying force and is attached to the guide device under the action of the surface tension of the liquid, or wherein spraying a liquid to the flexible electrode comprises: spraying a liquid toward the first section of the flexible electrode and the first surface of the guide device, such that the spraying force has a direction generally from the first section of the flexible electrode to the first surface of the guide device, or wherein the first section of the flexible electrode has a proximal end adjacent to the first engagement part and a distal end away from the first engagement part, and the first surface of the guide device has a proximal section adjacent to the first engagement part and a distal section away from the first engagement part, wherein spraying a liquid to the flexible electrode comprises: spraying a liquid toward the first section of the flexible electrode and the first surface of the guide device, such that the spraying force has a direction generally from the proximal end of the first section of the flexible electrode to the distal section of the first surface of the guide device.

4. The method according to claim 1, wherein the first surface of the guide device is configured as a smooth surface, or wherein the guide device is configured to have a needle-shaped portion.

5. The method according to claim 1, wherein the first engagement part is located at a first end of the flexible electrode, or wherein at least the first section of the flexible electrode is configured to be ribbon-shaped or filament-shaped, or wherein the first engagement part is configured to have a ring-shaped portion to enable the guide device to pass through the ring and engage with the first engagement part.

6. A method for guiding a flexible electrode, comprising:

applying a pulling force to a first end of the flexible electrode with a guide device to at least partially separate the flexible electrode from a flexible electrode fixing device;

spraying a liquid to the flexible electrode, such that at least a first section of the flexible electrode comes near to the guide device and is attached to the guide device; and guiding the flexible electrode with the guide device.

7. The method according to claim 6, wherein the first section of the flexible electrode is a portion of the flexible electrode adjacent to the first end, or wherein the guide device is configured to at least partially have a smooth surface to be attached by the flexible electrode, or wherein at least the first section of the flexible electrode is configured to be ribbon-shaped or filament-shaped, or wherein the guide device is configured to have a needle-shaped portion, or wherein the first end is configured to have a ring-shaped portion to enable the guide device to pass through the ring and apply a pulling force to the first end of the flexible electrode.

8. The method according to claim 6, wherein the liquid is sprayed in an atomized state or wherein the liquid comprises pure water.

9. The method according to claim 6, wherein the first section of the flexible electrode comes near to the guide device under the action of the spraying force and is attached to the guide device under the action of the surface tension of the liquid, or wherein spraying a liquid to the flexible electrode comprises: spraying a liquid toward the first section of the flexible electrode and the guide device, such that the spraying force has a direction generally from the first section of the flexible electrode to the guide device, or wherein the first section of the flexible electrode has a proximal end adjacent to the first end of the flexible electrode and a distal end away from the first end of the flexible electrode, and the guide device has a proximal section adjacent to the first end of the flexible electrode and a distal section away from the first end of the flexible electrode, wherein spraying a liquid to the flexible electrode comprises: spraying a liquid toward the first section of the flexible electrode and the guide device, such that the spraying force has a direction generally from the proximal end of the first section of the flexible electrode to the distal section of the guide device.

10. A method for guiding a flexible electrode, which comprises a first end configured to be adapted for engagement with a guide device and a first section connected to the first end, wherein the first section has a proximal end adjacent to the first end and a distal end away from the first end, wherein the method comprises:

engaging the guide device with the first end and causing the first section to be suspended from a fixing device via the distal end of the first section;

spraying a liquid to the flexible electrode in a direction generally from the first section to the guide device, such that at least the first section of the flexible electrode is attached to the guide device; and guiding the flexible electrode with the guide device.

11. The method according to claim 10, wherein the liquid is sprayed in an atomized state, or wherein the liquid comprises pure water.

12. The method according to claim 10, wherein the first section comes near to the guide device under the action of the spraying force and is attached to the guide device under the action of the surface tension of the liquid, or wherein the guide device has a proximal section adjacent to a first end of the flexible electrode and a distal section away from the first end of the flexible electrode, wherein spraying a liquid to the flexible electrode in a direction generally from the first section to the guide device comprises: spraying a liquid to the flexible electrode in a direction generally from the proximal end of the first section to the distal section of the guide device.

13. The method according to claim 10, wherein the guide device is configured to at least partially have a smooth surface to be attached by the flexible electrode, or wherein the flexible electrode is configured to be ribbon-shaped or filament-shaped, or wherein the guide device is configured to have a needle-shaped portion, or wherein the first end is configured to have a ring-shaped portion to enable the guide device to pass through the ring and engage with the first end.

14. A system for implanting a flexible electrode, comprising:

a flexible electrode fixing device located on one side of an implantation target, wherein the fixing device is configured to fix the flexible electrode to be implanted;

a driving device, which is so configured, that it can be positioned generally on an extension line from the implantation target to the fixing device and to drive a guide device for guiding the flexible electrode to move generally toward the target, wherein the driving device is further configured to drive the guide device to move to pull the flexible electrode after the guide device engages with a first engagement part of the flexible electrode fixed on the fixing device, thereby at least partially separating the flexible electrode from the fixing device; and a liquid spraying device positioned facing a first section in a portion of the flexible electrode, which is separated from the fixing device, and facing the guide device, wherein the liquid spraying device is configured to spray a liquid having a spraying force generally directed from the first section of the flexible electrode to the guide device, so that at least the first section of the flexible electrode is attached to the guide device under the action of a sprayed liquid, wherein the driving device is further configured to continue driving the guide device to move after at least the first section of the flexible electrode is attached to the guide device, thereby implanting the first engagement part of the flexible electrode and at least a portion of the first section adjacent to the first engagement part into the target.

15. The system according to claim 14, wherein the first section of the flexible electrode has a proximal end adjacent to the first engagement part and a distal end away from the first engagement part, and the guide device has a proximal section adjacent to the first engagement part and a distal section away from the first engagement part, wherein the liquid spraying device is further configured to:

spray a liquid having a spraying force generally directed from the proximal end of the first section of the flexible electrode to the distal section of the guide device, so that at least the first section of the flexible electrode is attached to the guide device under the action of a sprayed liquid.

16. The system according to claim 14, wherein the liquid spraying device is an atomized spray device, or wherein the liquid spraying device is further configured to spray a liquid comprising pure water or a solution suitable for the target, or wherein the guide device is configured to at least partially have a smooth surface to be attached by the flexible electrode, or wherein the guide device is so configured, that it can pass through the first engagement part, which is configured to be substantially ring-shaped, so as to engage with the first engagement part.

17. The system according to claim 14, wherein the guide device is so configured, that it can pass through the first engagement part, which is configured to be substantially ring-shaped, so as to engage with the first engagement part, wherein the guide device is configured to have a needle-shaped portion, which comprises a first portion having an outer diameter smaller than the inner diameter of the ring and a second portion having an outer diameter larger than the inner diameter of the ring, so that the first portion passes through the ring and the second portion cannot pass through the ring, thereby causing the guide device to engage with the first engagement part.

18. The system according to claim 17, wherein the driving device is further configured to continue driving the guide device to move after at least the first section of the flexible electrode is attached to the guide device, until the first portion and the second portion of the guide device at least partially enter the target, thereby implanting the first engagement part of the flexible electrode and at least a portion of the first section adjacent to the first engagement part into the target.

19. The system according to claim 14, wherein the fixing device comprises a support plate configured to detachably fix an electrode substrate on a surface thereof adjacent to the target, wherein the flexible electrode is adhered to the electrode substrate and thereby fixed on the support plate.

20. The system according to claim 19, wherein the electrode substrate has a hardness higher than the hardness of the flexible electrode, or wherein a plurality of flexible electrodes to be implanted are adhered side by side to the electrode substrate.

* * * * *